(12) United States Patent
Schmidt et al.

(10) Patent No.: US 10,519,080 B2
(45) Date of Patent: Dec. 31, 2019

(54) REMOVAL OF AROMATIC IMPURITIES FROM AN ALKENE STREAM USING AN ACID CATALYST, SUCH AS AN ACIDIC IONIC LIQUID

(71) Applicant: SAUDI BASIC INDUSTRIES CORPORATION, Riyadh (SA)

(72) Inventors: Roland Schmidt, Wiehl (DE); Shahid Azam, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/116,908

(22) PCT Filed: Feb. 5, 2015

(86) PCT No.: PCT/IB2015/050863
§ 371 (c)(1),
(2) Date: Aug. 5, 2016

(87) PCT Pub. No.: WO2015/118471
PCT Pub. Date: Aug. 13, 2015

(65) Prior Publication Data
US 2016/0355451 A1    Dec. 8, 2016

Related U.S. Application Data

(60) Provisional application No. 61/937,072, filed on Feb. 7, 2014.

(51) Int. Cl.
*C07C 7/148* (2006.01)

(52) U.S. Cl.
CPC ................ *C07C 7/14875* (2013.01)

(58) Field of Classification Search
None
See application file for complete search history.

(56) References Cited

U.S. PATENT DOCUMENTS

| | | |
|---|---|---|
| 2,860,173 A | 11/1958 | Jones |
| 3,094,568 A | 6/1963 | Hay |

(Continued)

FOREIGN PATENT DOCUMENTS

| | | |
|---|---|---|
| CN | 102387861 A | 3/2012 |
| CN | 102464539 A | 5/2012 |

(Continued)

OTHER PUBLICATIONS

Chinese Patent No. 102387861; Date of Publication: Mar. 21, 2012; Abstrat Only; 1 page.

(Continued)

*Primary Examiner* — Tam M Nguyen
(74) *Attorney, Agent, or Firm* — Cantor Colburn LLP (57) ABSTRACT

A process for the preparation of a chemical composition comprising an aromatic compound α in a concentration B by weight, based on the total weight of the chemical composition, comprising: a. providing the following reaction components: i. a chemical composition comprising the following: a) The aromatic compound α in a concentration A by weight based on the total weight of the chemical composition, and b) An olefin in an amount in an amount of about 50 to about 99.99 wt. %, based on the total weight of the chemical composition, and ii. An acid; and b. reacting the components to obtain the chemical composition comprising the aromatic compound α in a concentration B by weight based on the total weight of the chemical composition; wherein the concentration B is less than the concentration A.

20 Claims, 1 Drawing Sheet

(56) References Cited

U.S. PATENT DOCUMENTS

| | | |
|---|---|---|
| 3,129,256 A | 4/1964 | Hay et al. |
| 3,131,230 A | 4/1964 | Hervert |
| 3,631,120 A | 12/1971 | Eberly, Jr. |
| 4,016,218 A | 4/1977 | Haag et al. |
| 4,094,922 A | 6/1978 | Bartek et al. |
| 4,209,383 A | 6/1980 | Herout et al. |
| 4,243,828 A | 1/1981 | Kerr et al. |
| 4,764,440 A | 8/1988 | Jones et al. |
| 5,030,785 A | 7/1991 | Huss, Jr. et al. |
| 5,107,048 A | 4/1992 | Huss, Jr. et al. |
| 5,149,894 A | 9/1992 | Holtermann et al. |
| 5,171,915 A | 12/1992 | Forbus et al. |
| 5,210,350 A | 5/1993 | Solofo et al. |
| 5,491,208 A | 2/1996 | Tanaglia et al. |
| 5,648,579 A | 7/1997 | Kulprathipanja et al. |
| 5,731,101 A | 3/1998 | Sherif et al. |
| 5,750,455 A | 5/1998 | Chauvin et al. |
| 5,824,832 A | 10/1998 | Sherif et al. |
| 5,863,419 A | 1/1999 | Huff, Jr. et al. |
| 5,994,602 A | 11/1999 | Abdul-Sada et al. |
| 6,028,024 A | 2/2000 | Hirschauer et al. |
| 6,172,274 B1 | 1/2001 | Gosling |
| 6,969,693 B2 | 11/2005 | Sauvage et al. |
| 7,285,698 B2 | 10/2007 | Liu et al. |
| 7,304,198 B2 | 12/2007 | Wang et al. |
| 7,432,408 B2 | 10/2008 | Timken et al. |
| 7,432,409 B2 | 10/2008 | Elomari et al. |
| 7,476,774 B2 | 1/2009 | Umansky et al. |
| 7,495,144 B2 | 2/2009 | Elomari |
| 7,531,707 B2 | 5/2009 | Harris et al. |
| 7,745,674 B2 | 6/2010 | Boyer et al. |
| 7,732,651 B2 | 8/2010 | Driver et al. |
| 7,842,738 B2 | 11/2010 | Milligan et al. |
| 8,030,238 B2 | 10/2011 | Spano et al. |
| 8,101,810 B2 | 1/2012 | Boyer et al. |
| 8,124,821 B2 | 2/2012 | Elomari et al. |
| 8,319,000 B2 | 10/2012 | Hommeltoft |
| 2003/0060359 A1 | 3/2003 | Olivier-Bourbigou et al. |
| 2005/0154243 A1 | 7/2005 | Yeh et al. |
| 2006/0247479 A1 | 11/2006 | Barchha et al. |
| 2007/0100184 A1 | 5/2007 | Harmer et al. |
| 2007/0135656 A1 | 6/2007 | Hobbs et al. |
| 2007/0142686 A1 | 6/2007 | Campbell et al. |
| 2010/0160703 A1 | 6/2010 | Driver et al. |
| 2010/0179359 A1 | 7/2010 | Yeh et al. |
| 2011/0178355 A1 | 7/2011 | Fritz et al. |
| 2011/0319693 A1 | 12/2011 | Hommeltoft et al. |
| 2013/0150608 A1 | 6/2013 | Winsett et al. |

FOREIGN PATENT DOCUMENTS

| | | |
|---|---|---|
| EP | 0404179 B1 | 12/1990 |
| EP | 2338955 A1 | 6/2011 |
| FR | 2626572 | 8/1989 |
| FR | 2795403 A1 | 12/2000 |
| WO | 9420437 | 9/1994 |
| WO | 9850153 | 11/1998 |
| WO | 0041809 | 7/2000 |
| WO | 2012108861 A1 | 8/2012 |
| WO | 2013061336 A2 | 5/2013 |
| WO | 2015118469 A1 | 8/2015 |
| WO | 2015118470 A1 | 8/2015 |

OTHER PUBLICATIONS

Chinese Patent No. 102464539; Date of Publication: May 23, 2012; Abstract Only, 2 pages.

French Patent No. 2626572; Date of Publication: Aug. 4, 1989; Abstract Only, 1 page.

French Patent No. 2795403; Date of Publication: Dec. 29, 2000; Abstract Only, 1 page.

International Search Report for International Application No. PCT/IB2015/050863; dated May 8, 2015; 4 pages.

Written Opinion of the International Search Report for International Application No. PCT/IB2015/050863; dated May 8, 2015; 6 pages.

Hansmeier, A.R., "Ionic liquids as alternative solvents for aromatics extraction", University of Technology, 2010, 261 pages.

REMOVAL OF AROMATIC IMPURITIES FROM AN ALKENE STREAM USING AN ACID CATALYST, SUCH AS AN ACIDIC IONIC LIQUID

CROSS REFERENCE TO RELATED APPLICATIONS

This application is a 371 of International Application No. PCT/IB2015/050863, filed Feb. 5, 2015, which claims priority to U.S. Application No. 61/937,072, filed Feb. 7, 2014 both which are incorporated herein by reference in their entirety.

TECHNICAL FIELD

Disclosed herein is a process for the removal of aromatic impurities from an alkene stream using an acid catalyst. Also disclosed is a process for the preparation of downstream products preferably polymers and shaped bodies.

BACKGROUND

Alkenes, in particular α-olefins, have for a long time been desirable in the chemical industry. Due to the double bond, they can be converted into a number of other valuable compounds such as alcohols, aldehydes, ketones and organic halides, just to name a few. In polymerisation reactions they can be used as monomer or co-monomer and are particularly valuable in the production of plastics. For reasons of toxicity, environmental safety and production efficiency, it is desirable to produce an alkene stream with reduced content of certain aromatic compounds, in particular benzene. Reduction of content of certain aromatic compounds is also a concern in terms of compliance with various governmental environmental regulations. There remains a need in the prior art for methods for the reduction of the content of certain aromatic compounds, particularly benzene, in alkene streams.

SUMMARY

Disclosed, in various embodiments, are processes for the preparation of a chemical composition comprising an aromatic compound.

A process for the preparation of a chemical composition comprising an aromatic compound α in a concentration B by weight, based on the total weight of the chemical composition, includes: a. providing the following reaction components: i. a chemical composition comprising the following: a) The aromatic compound α in a concentration A by weight based on the total weight of the chemical composition, and b) An olefin in an amount in an amount of about 50 to about 99.99 wt. %, based on the total weight of the chemical composition, and ii. An acid selected from an acidic ionic liquid, a protic compound, an ammonium, an imidazolium, an anion selected from $AlCl_4^-$, $AlBr_4^-$, $AlI_4^-$, $BF_4^-$, $PF_6^-$, $CF_3SO_3^-$, $[(CF_3SO_2)_2N]^-$, toslyate, or a combination comprising at least one of the foregoing, or a combination comprising at least one of the foregoing; and b. reacting the components to obtain the chemical composition comprising the aromatic compound α in a concentration B by weight based on the total weight of the chemical composition; wherein the concentration B is less than the concentration A.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

The present application is generally based overcoming at least one of the problems encountered in the state of the art in relation to the reduction in the content of certain aromatic compounds in an alkene stream, in particular the reduction of benzene content in an alkene stream, particular where the alkene is an alpha olefin. This applies in particular to low concentrations of the aromatic compound, which should be removed in an industrial scale process.

Another problem is to provide an efficient and sustainable alkene source for producing downstream products and shaped bodies.

A further problem is to provide a method for the reduction of the content of an aromatic compound in an alkene stream, particularly where the alkene stream and the aromatic compound have a similar boiling point. This is particularly the case where the aromatic compound is benzene and the alkene comprises one or more selected from: hexene, heptene, octene, or a combination comprising at least one of the foregoing.

A further problem is to provide a method for the reduction of the content of an aromatic compound in an alkene stream, particularly under mild conditions, in particular low temperature and low pressure, in order to avoid undesired side reactions.

A contribution to solving at least one of the above described problems is made by a process for the preparation of a chemical composition comprising an aromatic compound α in a concentration B by weight, based on the total weight of the chemical composition, comprising:
a. providing the following reaction components:
  i. a chemical composition comprising the following:
    a) The aromatic compound α in a concentration A by weight based on the total weight of the chemical composition, and
    b) An olefin in an amount of about 50 to about 99.99 wt. %, preferably about 80 to about 99.99 wt. %, more preferably about 95 to about 99.99 wt. %, most preferably about 99 to about 99.99 wt. %, based on the total weight of the chemical composition, and
  ii. An acid selected from an acidic ionic liquid, a protic compound, an ammonium, an imidazolium, an anion selected from $AlCl_4^-$, $AlBr_4^-$, $AlI_4^-$, $BF_4^-$, $PF_6^-$, $CF_3SO_3^-$, $[(CF_3SO_2)_2N]^-$, toslyate, or a combination comprising at least one of the foregoing, or a combination comprising at least one of the foregoing; and
b. reacting the components to obtain the chemical composition comprising the aromatic compound α in a concentration B by weight based on the total weight of the chemical composition;
wherein the concentration B is less than the concentration A.

In one embodiment of the process, the olefin b) is an α-olefin.

In one embodiment of the process, the olefin b) is a $C_2$-$C_{20}$ olefin, preferably a $C_2$-$C_{15}$ olefin, more preferably a $C_4$-$C_{10}$ olefin.

In one embodiment of the process, the olefin b) is $C_6$-$C_{20}$ olefin, preferably a $C_6$-$C_{15}$ olefin, more preferably a $C_6$-$C_{10}$ olefin.

In one embodiment of the process, the concentration A is about 2 parts per million (ppm) to about 10 weight percent (wt. %), preferably in about 3 ppm to about 5 wt. %, more preferably about 4 ppm to about 1 wt. %, based on the total weight of the chemical composition i.

In one embodiment of the process, the ratio of A:B is about 1:0 to about 1:0.1, preferably about 1:0 to about 1:0.01, more preferably about 1:0.1 to about 1:001.

In one embodiment of the process, the aromatic compound is benzene.

In one embodiment of the process, a further olefin is present as a component of a), wherein the further olefin is different to the olefin b).

In one embodiment of the process, the further olefin is a $C_2$-$C_{20}$ olefin, preferably a $C_2$-$C_{15}$ olefin, more preferably a $C_4$-$C_{10}$ olefin.

In one embodiment of the process, the acid comprises an acidic ionic liquid.

In one embodiment of the process, the acid comprises a protic compound.

In one embodiment of the process, the acid comprises an ammonium.

In one aspect of this embodiment, the ammonium has the general formula $NR_4$, wherein R is hydrocarbon or hydrogen, and wherein each R can be the same as or different to the other R in the molecule.

In a further aspect of this embodiment, at least one R is alkyl, preferably methyl through hexyl, more preferably butyl.

In one embodiment of the process, the acid comprises an imidazolium.

In one aspect of this embodiment, the imidazolium has the general formula wherein $R_2$ is alkyl;
wherein each of $R_1$, $R_3$, $R_4$ is hydrocarbon or hydrogen;
wherein $R_1$, $R_2$, $R_3$, $R_4$ within a molecule can be the same as or different to each other.
In one aspect of this embodiment, $R_2$ is butyl.
In one aspect of this embodiment, $R_2$ is butyl and $R_1$, $R_2$ and $R_3$ have one of the following configurations:
a. $R_1$, $R_3$ and $R_4$ are hydrogen;
b. $R_1$ and $R_3$ are hydrogen and $R_4$ is alkyl, preferably methyl or ethyl, more preferably methyl;
c. $R_1$ and $R_4$ are hydrogen and $R_3$ is alkyl, preferably methyl or ethyl, more preferably methyl;
d. $R_4$ and $R_3$ are hydrogen and $R_1$ is alkyl, preferably methyl or ethyl, more preferably methyl.

In one embodiment of the process, the acid comprises an anion selected from $AlCl_4^-$, $AlBr_4^-$, $AlI_4^-$, $BF_4^-$, $PF_6^-$, $CF_3SO_3^-$, $[(CF_3SO_2)_2N]^-$, toslyate, or a combination comprising at least one of the foregoing, preferably $AlCl_4^-$, $AlBr_4^-$, $AlI_4^-$, $BF_4^-$, or a combination comprising at least one of the foregoing, more preferably $AlCl_4^-$.

In one embodiment of the process, the acid is present in step b. in a concentration of about 0.1 to about 50 wt. %, preferably about 0.5 to about 20 wt. %, more preferably about 1 to about 5 wt. %, based on the total weight of the reaction components.

In one embodiment of the process, the acid is present in step b. in a concentration of about 1 to about 20 wt. %, preferably about 2 to about 10 wt. %, more about 3 to about 5 wt. %.

In one embodiment of the process, the chemical composition i. is a homogeneous liquid.

In one embodiment of the process, the reaction b. is carried out at a temperature of about 0 to about 250° C., preferably about 0 to about 100° C., more preferably in about 10 to about 50° C.

A contribution to achieving at least one of the above mentioned objects is made by a process for the preparation of a downstream product comprising:
i. preparation of an alkene by a process as disclosed herein; and
ii. reaction of the alkene to form the downstream product.

In one embodiment of the process for the preparation of a downstream product, the downstream product is a polymer.

In one embodiment of the process for the preparation of a downstream product, the downstream product is a polyethene or a polypropene (e.g., polyethylene or polypropylene).

In one embodiment of the process for the preparation of a downstream product, the downstream product is converted into a shaped body.

A contribution to achieving at least one of the above mentioned objects is made by a process for the treatment of an olefin stream, preferably an α-olefin stream, in order to reduce the content of a certain aromatic compound α, preferably benzene.

In one embodiment, the content of the aromatic compound α is reduced by means of an alkylation reaction to yield an alkylated aromatic compound distinct from the aromatic compound α. In one aspect of this embodiment, the alkylated aromatic compound can differ from the aromatic compound α by a single additional alkylation or multiple additional alkylations. The alkylated aromatic compound preferably differs from the aromatic compound α by one, two or three additional alkylations. In one aspect of this embodiment, the product composition comprises at least two or more distinct alkylated aromatic compounds which can be distinct by virtue of a different number of alkyl groups, or different type of alkyl groups, or by a combination of both. In another aspect, at least 50 wt. %, preferably at least 90 wt. %, more preferably at least 99 wt. % of the alkylated aromatic product is composed of a single alkylation product.

In one embodiment, the reaction of the aromatic compound, preferably the alkylation reaction, is catalysed by an acid. In one aspect of this embodiment, a further catalyst, different from the acid catalyst, can be present.

The skilled person can choose the reaction conditions in any way he sees fit in order to increase the advantageous properties of the reaction.

It is preferred that the reaction be carried out in the liquid phase, preferably in a single homogeneous liquid phase.

It is preferred for the reaction to be carried out at a temperature of about 0 to about 250° C., preferably about 0 to about 200° C., more preferably about 0 to about 150° C.

It is preferred that the reaction be carried out at a pressure which allows a liquid phase reaction. In one embodiment, the reaction is carried out at a pressure of about 0.05 MegaPascals (MPa) to about 12 MPa (about 0.5 to about 120 bar), preferably about 0.05 MPa to about 6 MPa (about 0.5 to about 60 bar), more preferably about 0.05 MPa to about 0.5 MPa (0.5 to about 5 bar).

A contribution to achieving at least one of the above mentioned objects is made by a process for the treatment of a chemical composition comprising the following:
a) The aromatic compound α in a concentration A by weight based on the total weight of the chemical composition, and
b) An olefin in an amount of about 50 to about 99.99 wt. %, preferably about 80 to about 99.99 wt. %, more preferably about 95 to about 99.999 wt. %, most preferably about 99 to about 99.9999 wt. %, based on the total weight of the chemical composition, The olefin can be chosen according to the particular application. Preferred olefins are α-olefins and/or olefins which are employed as monomers and/or co-monomers in polymerisation reactions. Preferred α-olefins in this context are those comprising carbon atoms of about 2 to about 30, preferably about 2 to about 15, more preferably about 2 to about 8. Preferred α-olefins are ethene, propene, but-1-ene, pent-1-ene, hex-1-ene, hept-1-ene, oct-1-ene, non-1-ene, dec-1-ene and higher α-olefins. The preferred α-olefins are hex-1-ene, hept-1-ene or oct-1-ene.

The alkene stream can contain a single olefin or can comprise at least two or more distinct olefins. In one embodiment, at least 50 wt. %, more preferably at least 90 wt. %, most preferably at least about 99 wt. % of the chemical composition i) is a single alkene. In another embodiment, the chemical composition comprises at least 10 wt. %, preferably at least 15 wt. %, more preferably at least 20 wt. % of a first olefin and at least 10 wt. %, preferably at least 15 wt. %, more preferably at least 20 wt. % of a second olefin distinct from the first olefin.

In a further embodiment, the alkene stream contains more than distinct alkenes, preferably with at least one of those alkenes being a $C_6$-$C_{20}$ alkene, preferably a $C_6$-$C_{15}$ alkene, more preferably a $C_6$-$C_{10}$ alkene. In one aspect of this embodiment, the alkene stream comprises hex-1-ene, preferably about 50 to about 99 wt. %, more preferably about 65 to about 95 wt. %, most preferably about 75 to about 90 wt. %, based on the total weight of the alkene stream. In one aspect of this embodiment, the alkene stream comprises hept-1-ene, preferably about 1 to about 30 wt. %, more preferably about 3 to about 20 wt. %, most preferably about 8 to about 15 wt. %, based on the total weight of the alkene stream. In one aspect of this embodiment, the alkene stream comprises oct-1-ene, preferably about 0.1 to about 10 wt. %, more preferably about 0.5 to about 7 wt. %, most preferably in about 1 to about 5 wt. %, based on the total weight of the alkene stream. In one aspect of this embodiment, the alkene stream comprises alkene with more than 8 carbon atoms, preferably about 0.1 to about 10 wt. %, more preferably about 0.5 to about 7 wt. %, most preferably about 1 to about 5 wt. %, based on the total weight of the alkene stream. In one aspect of this embodiment, the aromatic compound α, which is preferably benzene, is present in the alkene stream in a concentration A of about 2 ppm to about 1000 ppm, preferably about 20 ppm to about 700 ppm, more preferably about 100 ppm to about 400 ppm. In one aspect of this embodiment, the aromatic compound is present in the product stream in a concentration B of about 0 ppm to about 1 ppm, preferably about 0.01 ppm to about 0.5 ppm, more preferably about 0.1 ppm to about 0.4 ppm.

The aromatic compound α can be chosen according to the particular application. Preferred aromatic compounds a are based on a benzene ring or on a naphthalene ring, preferably based on a benzene ring. The aromatic compound α can itself be singly alkylated multiply alkylated or not alkylated. The aromatic compound α is preferably not alkylated. Preferred aromatic compounds α are benzene, toluene, xylene, styrene, or a derivative of any of the preceding, or a mixture of at least two or more of the preceding, preferably benzene, or a combination comprising at least one of the foregoing. Preferred substituents of the aromatic compound α are halogen, preferably F, Cl, Br or I, or a combination comprising at least one of the foregoing, preferably F or Cl. Preferred isomers of xylene in this context are ortho, meta or para, or a combination of at least two or more thereof. The preferred aromatic compound α is benzene.

In one embodiment, the aromatic content of the composition i) consists of at least 50 wt. %, preferably at least 90 wt. %, more preferably at least about 99 wt. % of a single aromatic compound, based on the total weight of aromatic compounds in the composition i). In another embodiment, the aromatic content of the composition i) comprises at least 10 wt. %, preferably at least 15 wt. %, more preferably at least 20 wt. % of a first aromatic compound and at least about 10 wt. %, preferably at least about 15 wt. %, more preferably at least about 20 wt. % of a second aromatic compound, in each case based on the total weight of aromatic compounds in the composition i).

The acid ii. preferably catalyses the reaction which reduces the content of aromatic compound α in the composition i). The skilled person has knowledge of acids and their use as chemical catalysts. He can select any acid which he considers fit for improving the advantageous characteristics of the reaction.

Preferred acids are acidic ionic liquids. Preferred acidic ionic liquids comprise one or more salts in the liquid phase. A preferred ionic liquid is a liquid in which at least 0.1 mole percent (mol %), preferably at least about 1 mol %, more preferably at least about 10 mol % of the particles are electrically charged.

The acid preferably comprises one or more selected from: a protic compound, an acidic ionic liquid compound, a Bronsted acid, or a combination comprising at least one of the foregoing.

Preferred protic compounds in this context are compounds which are capable of donating at least one or more than one proton. The skilled person has knowledge of protic compounds and can select the protic compound in any way he sees fit in order to enhance the advantageous properties of the reaction.

In one aspect of this embodiment, the acid comprises at least one or more than one N—H bond, preferably present in a positive ion. In this context it is preferred that the acid comprise at least one or more than one cation selected from the following: ammonium or derivative thereof, imidazolium or derivative thereof, pyrazolium or derivative thereof, oxazolium or derivative thereof, pyridinium or derivative thereof, pyrolidinium or derivative thereof, isoxazolium or derivative thereof, thiazolium or derivative thereof, preferably ammonium or derivative thereof or imidazolium or derivative thereof, or a combination comprising at least one of the foregoing.

In one embodiment, the acid is cyclic, preferably comprising at least one N atom and preferably at least one N—H bond.

In one embodiment of the process, the acid comprises at least one ammonium.

In one aspect of this embodiment, the ammonium has the general formula $NR_4$, wherein R is hydrocarbon or hydrogen, and wherein each R can be the same as or different to the other R in the molecule. In further aspects of this embodiment, the ammonium can be primary, secondary or tertiary ammonium. Preferred hydrocarbons R are alkyl or aromatic, preferably alkyl. Alkyl groups R can be n-alkyl, iso-alkyl, tert-alkyl, preferably n-alkyl. Preferred alkyl groups R are methyl, ethyl, propyl butyl, pentyl or hexyl, preferably methyl or ethyl, more preferably ethyl.

In one embodiment of the process, the acid comprises an imidazolium.

In one aspect of this embodiment, the imidazolium has the general formula wherein $R_2$ is alkyl, preferably methyl or butyl, more preferably butyl;

wherein each of $R_1$, $R_3$, $R_4$ is hydrocarbon, preferably alkyl, or hydrogen;

wherein $R_1$, $R_2$, $R_3$, $R_4$ within a molecule can be the same as or different to each other.

In one embodiment, the imidazolium is singly substituted. $R_2$ is alkyl, preferably methyl or butyl, more preferably butyl. $R_1$, $R_3$ and $R_4$ are each hydrogen.

In one embodiment, the imidazolium is doubly substituted. $R_2$ is alkyl, preferably methyl or butyl, more preferably butyl. In one aspect of this embodiment, $R_1$ is a hydrocarbon, preferably alkyl, more preferably methyl or butyl, most preferably methyl; and $R_3$ and $R_4$ are hydrogen. In one aspect of this embodiment, $R_3$ is a hydrocarbon, preferably alkyl, more preferably methyl or butyl, most preferably methyl; and $R_1$ and $R_4$ are hydrogen. In one aspect of this embodiment, $R_4$ is a hydrocarbon, preferably alkyl, more preferably methyl or butyl, most preferably methyl; and $R_3$ and $R_1$ are hydrogen.

In one embodiment, the imidazolium is triply substituted. $R_2$ is alkyl, preferably methyl or butyl, more preferably butyl. In one aspect of this embodiment, $R_1$ and $R_3$ are hydrocarbon, preferably alkyl, more preferably methyl or butyl, most preferably methyl, and $R_1$ and $R_3$ can be the same as or different to each other; and $R_4$ is hydrogen. In one aspect of this embodiment, $R_1$ and $R_4$ are hydrocarbon, preferably alkyl, more preferably methyl or butyl, most preferably methyl, and $R_1$ and $R_4$ can be the same as or different to each other; and $R_3$ is hydrogen. In one aspect of this embodiment, $R_4$ and $R_3$ are hydrocarbon, preferably alkyl, more preferably methyl or butyl, most preferably methyl, and $R_4$ and $R_3$ can be the same as or different to each other; and $R_1$ is hydrogen.

In one embodiment, the imidazolium is four times substituted. $R_2$ is alkyl, preferably methyl or butyl, more preferably butyl. $R_1$ $R_3$, and $R_4$ are each hydrocarbon, preferably alkyl, more preferably methyl or butyl, most preferably methyl. $R_1$, $R_2$, $R_3$, and $R_4$ can be the same as or different to each other in the molecule.

Preferred imidazoliums are alkyl substituted imidazolium, wherein the alkyl groups are preferably one or more than one selected from: methyl, ethyl, propyl, butyl, pentyl, hexyl, preferably methyl or butyl, or a combination comprising at least one of the foregoing. The imidazolium is preferably substituted at one or more than one of the following position: 1 ($R_2$), 2 ($R_1$), 4 ($R_4$), 5 ($R_3$), preferably 1 ($R_2$) and/or 4 ($R_4$). Preferred imidazolium derivatives are dimethyl imidazolium, preferably 1,4-dimethyl imidazolium; di butyl imidazolium, preferably 1,4-dibutyl imidazolium; methyl imidazolium, preferably 1-methyl imidazolium; butyl imidazolium, preferably 1-butyl imidazolium; methyl-butyl imidazolium, preferably 1-methyl-4-butyl-imidazolium or 1-butyl-4-methyl imidazolium.

In one embodiment of the process, the acid comprises a coordinated Lewis acid. Preferred Lewis acids in this context are $AlCl_3$, $AlBr_3$, $AlI_3$, $BF_3$, $PF_5$, $SO_3$, preferably $AlCl_3$, or a combination comprising at least one of the foregoing. Preferred coordinating species in this context are $Cl^-$, $Br^-$, $I^-$, $F^-$, preferably $Cl^-$, or a combination comprising at least one of the foregoing.

In one embodiment of the process, the acid comprises an anion selected from $AlCl_4^-$, $AlBr_4^-$, $AlI_4^-$, $BF_4^-$, $PF_6^-$, $CF_3SO_3^-$, $[(CF_3SO_2)_2N]^-$, tosylate, or a combination comprising at least one of the foregoing, preferably from $AlCl_4^-$, $AlBr_4^-$, $AlI_4^-$, $BF_4^-$, or a combination comprising at least one of the foregoing, more preferably $AlCl_4^-$.

In one embodiment, acid comprises 1-butyl imidazolium aluminium tetra chloride.

In one embodiment, the process for the preparation of chemical composition, preferably an olefin stream, with a reduced content of a certain aromatic compound, preferably a reduced benzene content, is coupled to further subsequent reactions in order to obtain downstream products. Preferred downstream products are those obtained from polymerisation reactions, hydrogenation reactions, halogenation reactions, and other chemical functionalization reactions, preferably polymerisation reactions. Preferred monomeric downstream products are vinyl chloride monomer (VCM), ethylene glycol monomer (MEG), ethylene oxide (EO), acrylonitrile, butadiene, styrene, vinyl acetate monomer (VAM). Preferred oligomers are olefins, preferably linear olefins, preferably alpha olefins, preferably linear alpha olefins, such as 1-butene, 1-hexene, 1-octene, 1-decene, 1-dodecene, 1-tetradecene, 1-hexadecene or 1-octadecene. Preferred polymerisation reactions can be mono-polymerization reactions or co-polymerization reactions. Preferred polymerisation products are polythenes, substituted polythenes, polythene derivatives, polyvinyl chlorides, polyethylene glycols (PEG), acrylonitrile butadiene styrenes (ABS), polyvinyl acetates, poly olefins, preferably poly alpha olefins (PAO), styrene butadiene rubber (SBR), and other polymers comprising at least one of the above described monomers. Preferred polymers are polythenes or polythene derivatives. Preferred forms of polythene and its derivatives are ultra-high-molecular-weight polyethylene (UHMWPE), ultra-low-molecular-weight polyethylene (ULMWPE or PE-WAX), high-molecular-weight polyethylene (HMWPE), high-density polyethylene (HDPE), high-density cross-linked polyethylene (HDXLPE), cross-linked polyethylene (PEX or XLPE), medium-density polyethylene (MDPE), linear low-density polyethylene (LLDPE), low-density polyethylene (LDPE), or very-low-density polyethylene (VLDPE), chlorinated polyethylene (CPE), or combinations of at least two thereof, preferably HDPE, LLDPE or LDPE. Preferred functionalization products are aromatic or nonaromatic compounds, saturated or unsaturated compounds, ketones, aldehydes, esters, amides, amines, carboxylic acids, alcohols etc.

In one embodiment, the downstream products are further processed, particularly in the case where the downstream product is a polymer, particularly when it is polythene or a derivative thereof. In one embodiment, this further processing preferably involves formation of shaped objects such as plastic parts for electronic devices, automobile parts, such as bumpers, dashboards, or other body parts, furniture, or other parts or merchandise, or for packaging, such as plastic bags, film, or containers.

Figure 1:
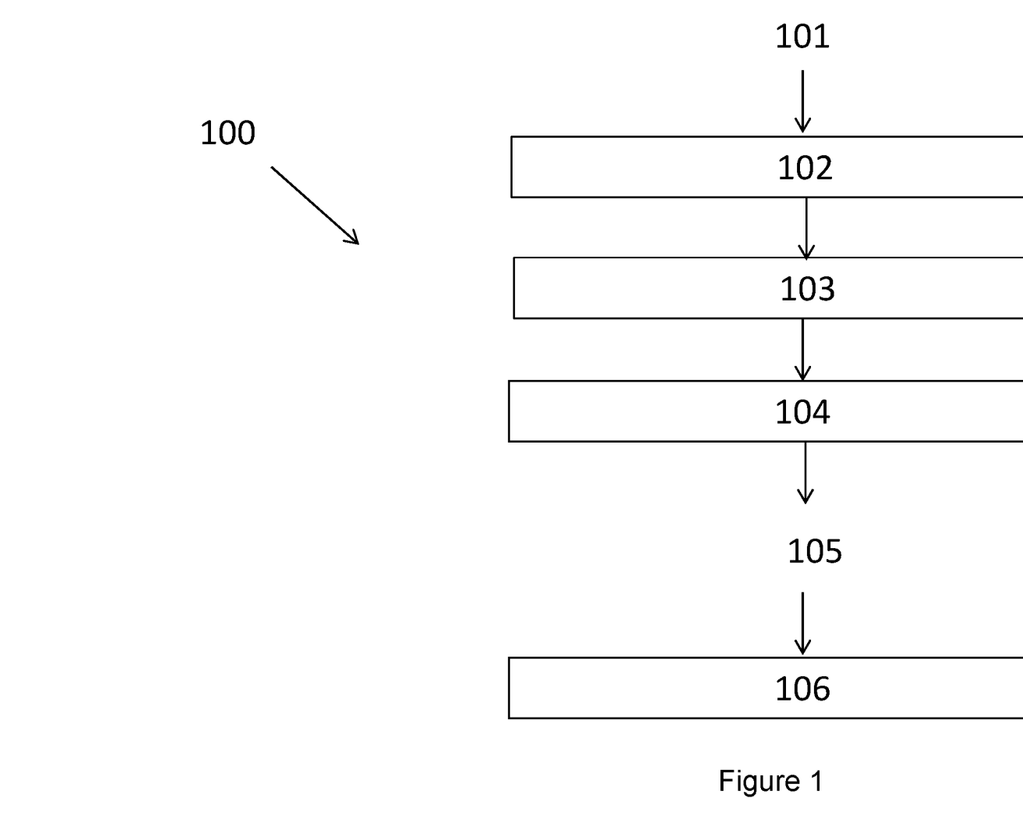
FIG. 1 is a schematic process flow diagram for the reduction in the content of certain aromatic compounds.

FIG. 1 shows a schematic process flow diagram 100 for the reduction in the content of certain aromatic compound α, preferably benzene, of a chemical composition, preferably an olefin stream, preferably an α-olefin stream, wherein the chemical composition enters the process with a content A of the aromatic compound 101 and exits the process with a content B of the aromatic compound α 105. The chemical composition 101 can first optionally undergo pre-processing 102, preferably one or more selected from the following: heating, cooling, filtration, distillation, or a combination comprising at least one of the foregoing. The chemical composition is then contacted with the acid 103, preferably comprising a protic compound, preferably comprising an ammonium and/or an imidazolium. The chemical composition is then optionally post-processed 104, preferably one or more selected from the following: heating, cooling, filtration, distillation, or a combination comprising at least one of the foregoing. Following the process to reduce the content of the aromatic compound α, the chemical composition 105 can optionally be used as a reactant in a further downstream reaction 106, preferably a polymerisation reaction, to produce a downstream product, preferably a poly α-olefin.

The content of aromatic compound α was determined using Capillary gas chromatography. Where the aromatic compound α was benzene, The ASTM international standard method ASTM D6229-06(2010) was used.

The following example is merely illustrative of the process disclosed herein and is not intended to limit the scope hereof

EXAMPLE

Example 1

100 milliliters (ml) of a hydrocarbon mixture with the composition given in column 2 of Table 1 was reacted with 10 ml 1-butyl imidazolium tetrachloro aluminate in a batch reactor (Parr 300 ml Autoclave Model 4566 Mini Benchtop reactor). The reaction was carried out at 1 bar, 20° C. for 10 minutes under stirring. The hydrocarbon mixture following reaction is given in column 3 of Table 1.

TABLE 1

| Hydrocarbon component | Reactant mixture | Product mixture |
| --- | --- | --- |
| Hex-1-ene | 82 wt. % | 82 wt. % |
| Hept-1-ene | 13 wt. % | 13 wt. % |
| Octo-1-ene | 2.5 wt. % | 2.5 wt. % |
| Alkenes with more than 8 carbon atoms | 2.5 wt. % | 2.5 wt. % |
| Benzene | 221.3 ppm | 0.2 ppm |

The process disclosed herein includes at least the following embodiments:

Embodiment 1

A process for the preparation of a chemical composition comprising an aromatic compound α in a concentration B by weight, based on the total weight of the chemical composition, comprising: a. providing the following reaction components: i. a chemical composition comprising the following: a) The aromatic compound α in a concentration A by weight based on the total weight of the chemical composition, and b) An olefin in an amount in an amount of about 50 to about 99.99 wt. %, based on the total weight of the chemical composition, and ii. An acid selected from an acidic ionic liquid, a protic compound, an ammonium, an imidazolium, an anion selected from $AlCl_4^-$, $AlBr_4^-$, $AlI_4^-$, $BF_4^-$, $PF_6^-$, $CF_3SO_3^-$, $[(CF_3SO_2)_2N]^-$, toslyate, or a combination comprising at least one of the foregoing, or a combination comprising at least one of the foregoing; and b. reacting the components to obtain the chemical composition comprising the aromatic compound α in a concentration B by weight based on the total weight of the chemical composition; wherein the concentration B is less than the concentration A.

Embodiment 2

The process according to Embodiment 1, wherein the olefin b) is an α-olefin.

Embodiment 3

The process according to any of the preceding embodiments, wherein the olefin b) is a $C_2$-$C_{20}$ olefin.

Embodiment 4

The process according to any of the preceding embodiments, wherein the concentration A is about 2 ppm to about 10 wt. % based on the total weight of the chemical composition i.

Embodiment 5

The process according to any of the preceding embodiments, wherein the ratio of concentration A: concentration B is about 1:0 to about 1:0.1.

Embodiment 6

The process according to any of the preceding embodiments, wherein the aromatic compound is benzene.

Embodiment 7

The process according to any of the preceding embodiments, wherein a further olefin is present as a component of a), wherein the further olefin is different to the olefin b).

Embodiment 8

The process according to Embodiment 7, wherein the further olefin is a $C_2$-$C_{20}$ olefin.

Embodiment 9

The process according to any of the preceding embodiments, wherein the acid comprises an acidic ionic liquid.

Embodiment 10

The process according to any of the preceding embodiments, wherein the acid comprises a protic compound.

Embodiment 11

The process according to any of the preceding embodiments, wherein the acid comprises an ammonium.

Embodiment 12

The process according to Embodiment 11, wherein the ammonium has the general formula $NR_4$, wherein R is hydrocarbon or hydrogen, and wherein each R can be the same as or different to the other R in the molecule.

Embodiment 13

The process according to Embodiment 12, wherein at least one R is alkyl.

Embodiment 14

The process according to any of the preceding embodiments, wherein the acid comprises an imidazolium.

Embodiment 15

The process according to Embodiment 14, wherein the imidazolium has the general formula wherein $R_2$ is alkyl; wherein each of $R_1$, $R_3$, $R_4$ is hydrocarbon or hydrogen; and
wherein $R_1$, $R_2$, $R_3$, $R_4$ within a molecule can be the same as or different to each other.

Embodiment 16

The process according to Embodiment 15, wherein $R_2$ is butyl.

Embodiment 17

The process according to Embodiment 15 or 16, wherein $R_2$ is butyl and $R_1$, $R_2$ and $R_3$ have one of the following configurations: a. $R_1$, $R_3$ and $R_4$ are hydrogen; b. $R_1$ and $R_3$ are hydrogen and $R_4$ is alkyl; c. $R_1$ and $R_4$ are hydrogen and $R_3$ is alkyl; and d. $R_4$ and $R_3$ are hydrogen and $R_1$ is alkyl.

Embodiment 18

The process according to any of the preceding embodiments, wherein the acid comprises an anion selected from $AlCl_4^-$, $AlBr_4^-$, $AlI_4^-$, $BF_4^-$, $PF_6^-$, $CF_3SO_3^-$, $[(CF_3SO_2)_2N]^-$, tosylate, or a combination comprising at least one of the foregoing.

Embodiment 19

The process according to any of the preceding embodiments, wherein the acid is present in step b. in a concentration of about 0.1 to about 50 wt. %, based on the total weight of the reaction components.

Embodiment 20

The process according to any of the preceding embodiments, wherein the acid is present in step b. in a concentration of about 1 to about 20 wt. %, based on the total weight of the reaction components.

Embodiment 21

The process according to any of the preceding embodiments, wherein the chemical composition i. is a homogeneous liquid.

Embodiment 22

The process according to any of the preceding embodiments, wherein the reaction b. is carried out at a temperature of about 0 to about 250° C.

Embodiment 23

A process for the preparation of a downstream product comprising: i. preparation of an alkene by a process according to any of preceding embodiments; and ii. reaction of the alkene to form the downstream product.

Embodiment 24

The process according to Embodiment 23, wherein the downstream product is a polymer.

Embodiment 25

The process according to Embodiment 23 or 24, wherein the downstream product is a polythene or a polypropene.

Embodiment 26

The process according to any of Embodiments 23 to 25, wherein the downstream product is converted into a shaped body.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A process for the preparation of a downstream product comprising:
   i. preparation of a chemical composition comprising an aromatic compound α in a concentration B by weight, based on the total weight of the chemical composition, comprising:
      a. providing the following reaction components:
         i. a chemical composition comprising the following:
            a) the aromatic compound α in a concentration A by weight based on the total weight of the chemical composition, and
            b) an olefin in an amount of about 50 to about 99.99 wt. %, based on the total weight of the chemical composition, wherein the olefin is a $C_4$ to $C_{10}$ olefin, and
         ii. an acid selected from an acidic ionic liquid, a protic compound, an ammonium, an imidazolium, an anion selected from $AlCl_4^-$, $AlBr_4^-$, $AlI_4^-$, $BF_4^-$, $PF_6^-$, $CF_3SO_3^-$, $[(CF_3SO_2)_2N]^-$, tosylate, or a combination comprising at least one of the foregoing, or a combination comprising at least one of the foregoing; and
      b. reacting the components to obtain the chemical composition comprising the aromatic compound α in a concentration B by weight based on the total weight of the chemical composition, wherein the chemical composition comprises an alkene;
   wherein the concentration B is less than the concentration A, and
   wherein the concentration B is 0.1 to 0.4 ppm; and
   ii. reaction of the alkene to form the downstream product;
   wherein the downstream product has a reduced benzene content of greater than 90%.

2. The process according to claim 1, wherein the concentration A is about 2 ppm to about 10 wt. % based on the total weight of the chemical composition i.

3. The process according to claim 1, wherein the ratio of concentration A: concentration B is about 1:0 to about 1:0.1.

4. The process according to claim 1, wherein the aromatic compound α is benzene.

5. The process according to claim 1, wherein a further olefin is present as a component of a), wherein the further olefin is different to the olefin b), and wherein the further olefin is a $C_2$-$C_{20}$ olefin.

6. The process according to claim 1, wherein the acid comprises an acidic ionic liquid or wherein the acid comprises a protic compound.

7. The process according to claim 1, wherein the acid comprises an ammonium, and wherein the ammonium has the general formula $NR_4$, wherein R is hydrocarbon or hydrogen, and wherein each R can be the same as or different to the other R in the molecule.

8. The process according to claim 1, wherein the acid comprises an imidazolium.

9. The process according to claim 8, wherein the imidazolium has the general formula wherein $R_2$ is alkyl;
wherein each of $R_1$, $R_3$, $R_4$ is hydrocarbon or hydrogen;
wherein $R_1$, $R_2$, $R_3$, $R_4$ within a molecule can be the same as or different to each other; and
wherein $R_2$ is butyl and $R_1$, $R_3$ and $R_4$ have one of the following configurations:
   a. $R_1$, $R_3$ and $R_4$ are hydrogen;
   b. $R_1$ and $R_3$ are hydrogen and $R_4$ is alkyl;
   c. $R_1$ and $R_4$ are hydrogen and $R_3$ is alkyl; and
   d. $R_4$ and $R_3$ are hydrogen and $R_1$ is alkyl.

10. The process according to claim 1, wherein the acid comprises an anion selected from $AlCl_4^-$, $AlBr_4^-$, $AlI_4^-$, $BF_4^-$, $PF_6^-$, $CF_3SO_3^-$, $[(CF_3SO_2)_2N]^-$, tosylate, or a combination comprising at least one of the foregoing.

11. The process according to claim 1, wherein the acid is present in step b. in a concentration of about 0.1 to about 50 wt. %, based on the total weight of the reaction components.

12. The process according to claim 1, wherein the chemical composition i. is a homogeneous liquid.

13. The process according to claim 1, wherein the reaction b. is carried out at a temperature of about 0 to about 250° C.

14. The process according to claim 1, wherein the downstream product is a polymer.

15. The process according to claim 1, wherein the downstream product is a polythene or a polypropene.

16. The process according to claim 1, wherein the olefin b) is present in an amount of about 80 to about 99.99 wt. %, based on the total weight of the chemical composition.

17. A process for the preparation of a downstream product comprising:
    a. reacting the following reaction components to obtain an alkene comprising an aromatic compound α in a concentration B by weight based on the total weight of the alkene:
        i. a chemical composition comprising the following:
            a) the aromatic compound α in a concentration A by weight based on the total weight of the chemical composition, and
            b) an olefin in an amount of about 50 to about 99.99 wt. %, based on the total weight of the chemical composition, wherein the olefin is a $C_2$ to $C_8$ olefin, and
        ii. an acid selected from an acidic ionic liquid, a protic compound, an ammonium, an imidazolium, an anion selected from $AlCl_4^-$, $AlBr_4^-$, $AlI_4^-$, $BF_4^-$, $PF_6^-$, $CF_3SO_3^-$, $[(CF_3SO_2)_2N]^-$, tosylate, or a combination comprising at least one of the foregoing, or a combination comprising at least one of the foregoing, wherein the concentration B is less than the concentration A; and
    b. reacting of the alkene to form the downstream product; wherein the downstream product has a reduced benzene content of greater than 90%.

18. The process according to claim 17, wherein the concentration B is 0.1 to 0.4 ppm.

19. The process according to claim 18, wherein the aromatic compound α is benzene.

20. The process according to claim 17, wherein the olefin b) is present in an amount of about 80 to about 99.99 wt. %, based on the total weight of the chemical composition.

* * * * *